United States Patent [19]
Klapper et al.

[11] Patent Number: 5,697,782
[45] Date of Patent: Dec. 16, 1997

[54] ORTHODONTIC DEVICE AND METHOD FOR CORRECTING OVERBITE AND UNDERBITE

[76] Inventors: Lewis Klapper, 744 Falls Cir., Lake Forest, Ill. 60045; Richard George, 930 Burridge Ct., Libertyville, Ill. 60048

[21] Appl. No.: 644,848

[22] Filed: May 9, 1996

[51] Int. Cl.$^6$ .................................................. A61C 7/36
[52] U.S. Cl. ........................ 433/19; 433/21; 433/24
[58] Field of Search ............................ 433/18, 19, 21, 433/22, 24

[56] References Cited

U.S. PATENT DOCUMENTS

| | | | |
|---|---|---|---|
| 3,508,332 | 4/1970 | Armstrong | 433/21 |
| 3,618,214 | 11/1971 | Armstrong | |
| 3,654,702 | 4/1972 | Kelly, Jr. | |
| 3,798,773 | 3/1974 | Northcutt | |
| 4,074,433 | 2/1978 | Nelson | 433/19 |
| 4,416,626 | 11/1983 | Bellavia | 433/7 |
| 4,551,095 | 11/1985 | Mason | 433/19 |
| 4,708,646 | 11/1987 | Jasper | 433/19 |
| 4,815,968 | 3/1989 | Keller | 433/7 |
| 5,312,247 | 5/1994 | Sachdeva et al. | 433/7 |
| 5,352,116 | 10/1994 | West | 433/19 |
| 5,435,721 | 7/1995 | Vogt | 433/19 |
| 5,443,384 | 8/1995 | Franseen et al. | 433/18 |

FOREIGN PATENT DOCUMENTS

| | | | |
|---|---|---|---|
| 2222950 | 3/1990 | United Kingdom | 433/19 |

OTHER PUBLICATIONS

"Mandibular Protraction Appliances for Class II Treatment", Carlos Martins Coelho Filho, DDS, MSD—JCO (May, 1995), vol. XXIX, No. 5, pp. 319-335.

*Primary Examiner*—Cary E. O'Connor
*Attorney, Agent, or Firm*—Welsh & Katz, Ltd.

[57] ABSTRACT

An orthodontic device is worn in a mouth of a patient and is attached between an upper attachment portion secured to the maxillary teeth and a lower attachment portion secured to the mandibular teeth such that the device is proximal a cheek of the patient. The device is formed from a single flexible resilient spring element having a generally curved body portion where the body portion is defined to lie in a plane relative to a plane defined by the cheek of the patient. The spring element has first and second oppositely disposed end portions where the first end portion is configured to directly attach to the upper attachment portion. The second end portion is configured to directly attach to the lower attachment portion. The spring element produces an applied force between the upper and lower attachment operative to displace the maxillary teeth relative to the mandibular teeth. The first end portion includes a primary bend that is disposed substantially within the plane of the body portion and operative to vary the effective length of the spring element where the variation in the effective length of the spring element varies the applied force directed to the maxillary and mandibular teeth. The second end portion terminates in a loop configured to attach to the lower attachment portion.

29 Claims, 3 Drawing Sheets

ORTHODONTIC DEVICE AND METHOD FOR CORRECTING OVERBITE AND UNDERBITE

BACKGROUND OF THE INVENTION

The present invention relates generally to orthodontic devices for treating various malocclusions including protrusion and retrusion of the upper teeth relative to the lower teeth.

A variety of malocclusions have been corrected with conventionally available orthodontic appliances so that an appropriate alignment is established for the upper teeth, for the lower teeth, and between the upper and lower teeth. Early efforts involved the application of orthodontic appliances to the teeth in conjunction with elastic (rubber) bands to apply appropriate forces to the orthodontic appliances between the upper and lower jaws. Removable head gear for interacting with the teeth is also known to achieve desired movements. Although these techniques have provided satisfactory results, they were found to be subject to certain disadvantages.

One disadvantage of such orthodontic systems is that satisfactory results can only be obtained if a particular device is properly worn. Elastic bands and head gear are easily removed by the patient, thus limiting their overall effectiveness. Head gear has the further disadvantage that since it contacts the neck, it is cosmetically undesirable and therefore less likely to be extensively worn.

Another disadvantage of such orthodontic systems is that they can produce undesirable side effects resulting from undesirable forces that may be applied to the orthodontic appliance in addition to those forces which are desired for an effective treatment to take place. These undesirable forces are most prevalent with elastic bands, at times resulting in tooth extrusion and bite opening. Head gear can also result in tooth extrusion. Elastic bands further have the disadvantage of delivering forces that can decay over time, as the elastic elements stretch and fatigue.

Various devices have been developed in an effort to improve upon the elastic bands and head gear of conventional orthodontic appliances. One such attempt involves the use of spring operated devices, primarily used to replace the elastic bands. Such devices are disclosed for example, in U.S. Pat. No. 3,618,214 (Armstrong), and U.S. Pat No. 5,352,116 (West). Generally, such devices employ springs to establish tensions similar to those established by elastic bands. However, in practice, the devices tend to produce relatively severe and undesirable side effects leading to unwanted tooth extrusion and bite opening. Moreover, most available spring-operated devices are removable (much like the elastic bands they replace), and are often not worn, lost, or broken. For those spring-operated devices that are not removable, it is often extremely difficult to clean around such devices. In either case, such devices tend to be bulky, making it difficult for patients to speak and eat with the appliances in place.

Another orthodontic device that has found acceptance is the so-called "bit jumping" appliance. Such appliances are disclosed, for example, in U.S. Pat. No. 3,798,773 (Northcutt), U.S. Pat. No. 4,551,095 (Mason), and U.S. Pat. No. 4,708,646 (Jasper).

All except U.S. Pat. No. 4,708,646 variations of a device generally known as the "Herbst" device, and include a metal cylinder containing a plunger that is attachable to and between the orthodontic appliances (braces) fixed to the patient's upper and lower teeth. Such devices are rigidly attached to the associated orthodontic appliances and as a result, cannot be removed by the patient. However, because of their rigid attachment, it is not uncommon for such devices to become damaged, or to cause damage to the orthodontic appliances to which they are attached. Primarily, this results from the lack of flexibility of the devices and the relatively large forces that are produced as the patient's jaws are closed in the normal course.

U.S. Pat. No. 4,708,646 replaces the conventional Herbst device with an elastic element comprised of a spring surrounded by a rubber core and having metal end caps for attachment to and between the orthodontic appliances associated with the patient's upper and lower teeth. In use, the elastic element tends to produce extremely high forces, similar to the Herbst device, and is highly susceptible to breakage. Breakage primarily results from the ability of the device to swivel about its attachment points, producing significant flexure. This permits the device at times, to become caught between the patient's upper and lower teeth. Separation of the end caps from the connecting spring and cover is quite common as a result. Additionally, such devices produce heavy intermittent forces when the upper and lower teeth are touching and virtually no force when the mouth is resting with the upper and lower teeth slightly apart.

U.S. Pat. No. 5,435,721 (Vogt) discloses a unitary element in the form of a substantially flat plate having integral end portions. The flat elongated plate attaches to upper and lower appliances using lengths of wire and stop balls and requires a keyed wire and end portion apertures to prevent twisting. Although this device may be effective to alter teeth alignment, its multiple parts make installation cumbersome. Additionally, to accommodate a normal range of required force, at least nine different lengths of the flat plate in a variety of widths and thicknesses would be needed. This would require an extensive and expensive inventory. Further, this device uses wire having a square cross-section, and the wire must be keyed to the shape of the aperture in the end portion of the flat plate. As a result, the device would not function properly when used with upper and lower round archwires in situations where the lower arch needs to be brought forward by allowing movement about a round wire, rather than about a square wire. The archwires must be removed and reinstalled in order to place these appliances.

Consequently, the need remains to provide a device for applying appropriate continuous forces to achieve the movements that are desired for a particular treatment, and to provide devices which are less susceptible to the disadvantages of improper usage and breakage. Additionally, a need exists for a device which is easy to install without removing the archwires, and which is comfortable for the patient to wear.

Accordingly, it is an object of the present invention to substantially overcome the above-described problems.

It is another object of the present invention to provide a novel orthodontic device that attaches to existing appliances without additional ties, ligatures, or pins.

It is a further object of the present invention to provide a novel orthodontic device and method that permits adjustment after installation.

It is also an object of the present invention to provide a novel orthodontic device that can be adjusted to vary the force applied to the teeth.

It is still an object of the present invention to provide a novel orthodontic device that lies in the plane of the patient's cheek and remains in that plane during full movement of the patient's mouth and does not protrude into the cheek or catch under the appliance or brackets.

It is yet another object of the present invention to provide a novel orthodontic device requiring a small number of variations in size to accommodate all patients.

It is yet a further object of the present invention to provide an orthodontic device that is comfortable to wear and permits the patient to easily clean around the device to practice proper hygiene.

It is another object of the present invention to provide an orthodontic device that applies a substantial continuous force over a wide range of mandibular movements.

SUMMARY OF THE INVENTION

The disadvantages of present orthodontic devices and methods are substantially overcome with the present invention by providing a novel orthodontic device and method for correcting overbite and underbite.

The present orthodontic device has significant features and advantages over known orthodontic devices. The device is especially easy to remove and insert and requires no removal or manipulation of existing hardware. The device is a single unitary spring body that attaches to existing hardware without use of any connecting wires, pins, stop balls, ligatures and the like. Additionally, no keying is required to prevent the device from twisting and turning, as is required in some other prior art devices. Since the device is essentially a unitary wire spring element requiring no additional connecting hardware, the device presents a minimal profile for trapping food. Accordingly, the device promotes proper hygiene and is easy to keep clean.

The novel orthodontic device attaches between the upper and lower teeth and does not pass through the imaginary line directly connecting the teeth. Thus, the device does not impinge upon the soft tissue of the mouth or upon the appliance. Since the device flexes during mandibular movement in a plane substantially parallel to the plane of the patient's cheek, the device does not protrude into the cheek. This significantly increases user comfort.

The novel orthodontic device is also cost-effective. Only three sizes or models are required to accommodate all patients from children to adults. Therefore, inventory burden is minimal. Additionally, the adjustment time is minimal as the orthodontist need only remove the device from the patient's mouth, perform the necessary "bending" adjustments, and reinsert the device between the upper and lower attachment points. This increases the orthodontist's efficiency.

The device provides a substantially continuous force throughout a wide range of mandibular movement, except at the extreme widest opening. The force applied by the device is easily adjusted by the orthodontist by bending the device to alter its effective length. A decrease in the effective length decreases the applied force and conversely, an increase in the effective length increases the applied force.

The novel orthodontic device applies translational force between the upper and lower teeth and reduces or eliminates rotational or "tipping" force about the tooth to which the device is attached. The longitudinal force is directed forwardly and backwardly relative to the patient's face. Thus, the teeth to which the novel device is attached do not require stabilization with an archwire attached to adjacent teeth. This permits attachment of the device where the primary teeth are being lost and replaced by permanent teeth.

More specifically, the orthodontic device for correcting overbite and underbite according to the present invention is worn in a mouth of a patient and is attached between an upper attachment means secured to the maxillary teeth and a lower attachment means secured to the mandibular teeth such that the device is proximal a cheek of the patient.

The device is formed from a single flexible resilient spring element having a generally curved body portion where the body portion is defined to lie in a plane relative to a plane defined by the cheek of the patient. The spring element has first and second oppositely disposed end portions where the first end portion is configured to directly attach to the upper attachment means. The second end portion is configured to directly attach to the lower attachment means.

The spring element produces an applied force between the upper and lower attachment means operative to displace the maxillary teeth relative to the mandibular teeth. The first end portion includes a primary bend that is disposed substantially within the plane of the body portion and operative to vary the effective length of the spring element where the variation in the effective length of the spring element varies the applied force directed to the maxillary and mandibular teeth. The second end portion terminates in a loop configured to attach to the lower attachment means.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

DETAILED DESCRIPTION OF THE INVENTION

Figure 1:
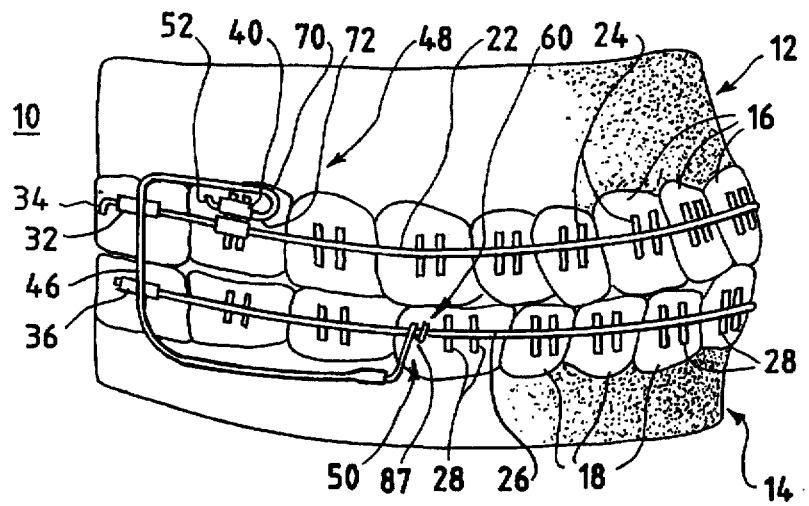
FIG. 1 is a side elevational view of a specific embodiment according to the present invention showing a spring element operatively attached to the teeth, as viewed from the side of a patient's mouth.

Referring now to FIG. 1, an orthodontic device 10 for correcting underbite and overbite is shown generally. The device 10 is shown operatively associated with an upper jaw 12 and a lower jaw 14 of a hypothetical patient. Upper teeth 16 are associated with the upper jaw 12 and lower teeth 18 are associated with the lower jaw 14. The novel orthodontic device 10 is attached between the upper or maxillary teeth 16 and the lower or mandibular teeth 18 to effect displacement of the upper teeth relative to the lower teeth.

In the illustrated embodiment, a substantially conventional upper archwire 22 is shown attached to the upper teeth 16. A plurality of vertical spaced-apart supports 24 are attached to the outer surface of each of the upper teeth 16 using bonding techniques or a suitable chemical adhesive, as is known in the art. The upper archwire 22 is appropriately interconnected between each of the vertical supports 24 using known conventional methods. A lower archwire 26 is similarly attached to the lower teeth 18 via corresponding spaced-apart vertical supports 28 attached to the lower teeth. Alternately, the vertical supports 24 and 28 may be replaced with known bands which surround each tooth.

The upper archwire 22 is received through an upper archwire molar tube 32 that is affixed to a molar of the upper teeth 16. An end 34 of the upper archwire 22 protrudes through the open end of the upper archwire molar tube 32 and is bent so as to lock the archwire in place in a conventional manner. The lower archwire 26 is secured in a similar fashion to a lower archwire molar tube 36. Such construction and attachment may employ any variety of known techniques.

The upper archwire molar tube 32 may be disposed on the first or second molar while an auxiliary molar tube 40 may be disposed on the first molar, as is dictated by the configuration of the patient's teeth 16 and 18 and the degree and type of movement desired. Alternately, the auxiliary molar tube 40 may be formed with or may be attached to the upper archwire molar tube 32, as is known in the art. Inclusion of the auxiliary molar tube 40 is conventional practice. The auxiliary molar tube 40 is typically present even if it is not used and is defined to be existing attachment hardware. The orthodontic device 10 is directly attached to the auxiliary molar tube 40, as will be described hereinafter. Note that in FIG. 1, the third molar is not shown.

Figure 2A:
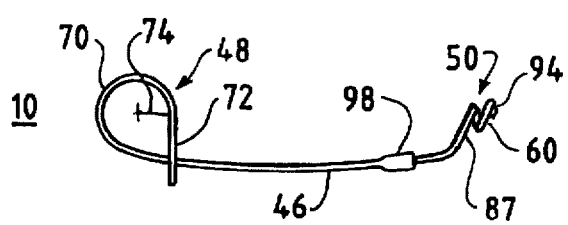
FIG. 2A is an side elevational view of a specific embodiment of a spring element.
Figure 2B:
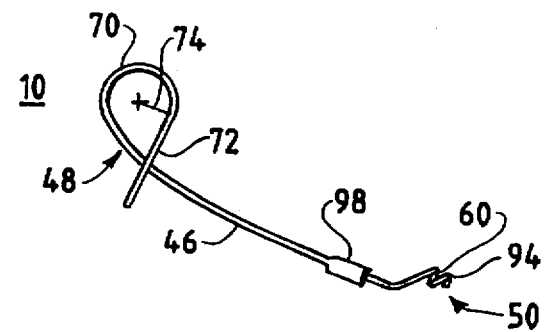
FIG. 2B is an side elevational view of the spring element of FIG. 2A tilted and viewed along the plane of a loop which terminates the second end of the spring element.

Referring now to FIGS. 1, 2A, and 2B, FIGS. 2A–2B illustrate the orthodontic device 10 in a relaxed or non-operative position when removed from the patient's mouth. The orthodontic device 10 is a single flexible resilient spring element having a generally curved body portion 46 that is defined to lie in a plane relative to a plane defined by the cheek of the patient. The term "spring element 10" will be used interchangeably with the term "orthodontic device" since the device is a unitary device.

Preferably the plane of the body portion 46 is adjusted so that the device 10 is disposed in a plane substantially parallel to the plane defined by the cheek of the patient. This provides several advantages which will be described in greater detail hereinafter.

The spring element 10 has a first end portion 48 and second end portion 50 oppositely disposed from the first end portion. The first end portion 48 is configured to directly attach to the auxiliary molar tube 40 via direct insertion into the tube.

Preferably, the spring element 10 is formed from stranded or braided wire. However, a suitable solid wire may be used. The spring element 10 has a uniform cross-sectional diameter along its length. Preferably, the diameter of the spring element 10 is about 0.050 inches and is substantially circular. However, the spring element 10 may have any suitable diameter sufficient to be received within the existing auxiliary molar tube 40. The spring element 10 may be formed from nickel titanium alloy, nickel chrome alloy, stainless steel, or any other suitable metal. The spring element 10 is resilient but may be permanently deformed by the orthodontist by bending the wire past its elastic limit. Once in a permanently deformed configuration, subsequent flexing of the spring element 10 within its elastic range results in resilient flexing of the spring element so that a preselected amount of substantially continuous force is applied to the upper and lower teeth 16 and 18, respectively. The spring element 10 may be coated with a plastic or rubber coating for aesthetic reasons.

However, the spring element 10 is not limited to metal construction. Alternately, a suitable thermoplastic or fiberglass material may be used. Permanent deformation of the thermoplastic material may be performed using heating techniques after the orthodontic device 10 has been removed from the patient's mouth, as is known in the art.

Figure 3:
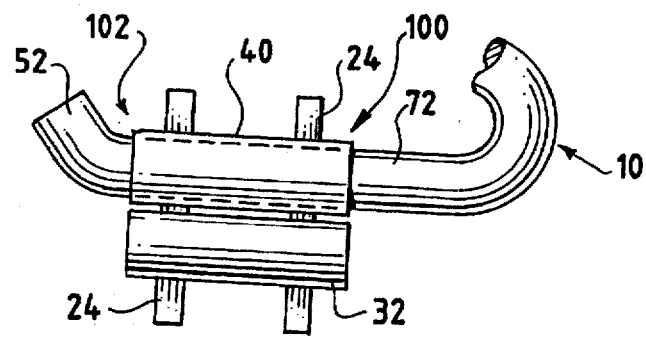
FIG. 3 is an enlarged side elevational view of the spring element of FIG. 1 particularly showing direct attachment of the spring element to an auxiliary molar tube.

Referring now to FIGS. 1 and 3, FIG. 3 shows an enlarged view of the spring element 10, the upper archwire molar tube 32, and the auxiliary molar tube 40. In this illustrated embodiment, the upper archwire molar tube 32 is disposed on the same tooth as the auxiliary molar tube 40. Since the spring element 10 has a uniform cross-sectional shape, it is easily received within the auxiliary molar tube 40. An end 52 of the spring element 10 protruding through the auxiliary molar tube 40 is bent so as to lock the spring element in place. This facilitates quick and convenient removal and attachment. To remove the spring element 10, the end 52 protruding through the auxiliary molar tube 40 is simply unbent and removed from within the tube. This is a significant improvement over conventional devices which are often permanently secured around the archwires requiring time-consuming removal of the archwires.

Many prior art devices are permanently secured to the archwire by separate wires and various forms of pins and ligatures. Some devices include an aperture through which the archwire pass. To remove such a device, the archwire must be removed from the teeth. This is extremely time-consuming and cumbersome. Additionally, the patient is inconvenienced unnecessarily.

Referring now to FIGS. 1, and 2A–2B, the second end portion 50 terminates in a loop 60 configured to attach to the lower archwire 26. With the first end portion 48 directly attached to auxiliary molar tube 40 and the loop 60 of the second end portion 50 attached about the lower archwire 26, the resiliency of the spring element 10 creates a translational force that is applied to the teeth tending to backwardly displace the upper teeth 16 and forwardly displace the lower teeth 18. This corrects an overbite condition, which accounts for a majority of patient malocclusions. However, to correct an underbite condition, the attachment position of the spring element 10 is simply reversed. That is, the first end portion 48 of the spring element 10 is attached to an auxiliary molar tube disposed on a bottom molar while the second end portion 50 is attached via the loop to the upper archwire 22. Such a configuration tends to forwardly displace the upper teeth 16 and backwardly displace the lower teeth 18 to correct an underbite.

It may be seen that the orthodontic device 10 is truly a unitary device. That is, it does not require any connectors, pins, ligatures, ball stops and the like. The auxiliary molar tube 40 is typically part of the orthodontic hardware, even if it is not utilized. Thus, to implement the device 10 in a standard and typical orthodontic setting, only the spring element 10 need be added. Virtually all known "push-type" orthodontic devices use some form of additional connector such as ball stops and connecting wires to attach the device.

Additionally, no "keying" is necessary to prevent twisting and turning of the device 10, as is required in prior art devices, such as in the device described above in the Vogt patent. The orthodontic device 10 maintains its orientation within the patient's mouth and does not impinge upon the cheek or upon the soft tissue of the mouth, as will be described in greater detail hereinafter.

The first end portion 48 of the spring element 10 has a primary bend 70 which is disposed substantially within the plane of the body portion 46. In the operative position, shown in FIG. 1, the primary bend 70 preferably does not cross over itself, as is shown in FIGS. 2A and 2B. However, there may be an additional bend or helix (not shown) in the body portion 48 when space in the mouth is very limited. The primary bend 70 includes a relatively straight segment 72 which is received through the auxiliary molar tube 40. The arc or a radius of curvature 74 of the primary bend 70 is operative to vary the effective length of the spring element 10. The smaller the radius of curvature 74, the smaller the effective length of the spring element 10. Conversely, the greater the radius of curvature 74, the greater the effective length of the spring element 10. Although the actual length of the material forming the spring element 10 remains constant for a given selected size or model, regardless of how it is bent, the effective length is a measure of the way in which the spring element 10 may be resiliently deformed with respect to the amount of force produced between the attachment points (e.g., the first end portion 48 and the second end portion 50). The effective length is also a measure of how that force is applied over a wide range of jaw movement.

With the straight segment 72 received within the auxiliary molar tube 40 and the loop 60 attached about the lower archwire 26, as shown in FIG. 1, it can be seen that as the primary loop 70 is made "tighter" (i.e., the radius of curvature 74 is decreased), the amount of force applied to the teeth 16 and 18 is increased, due in part, to the spring-like resistance of the spring element 10. Conversely, it can be seen that as the primary loop 70 is "relaxed" (i.e., the radius of curvature 74 is increased), the amount of force applied to the teeth 16 and 18 is reduced.

The fact that a change in the effective length of the spring element 10 varies the force applied to the teeth 16 and 18 is a very significant feature of the present orthodontic device. This permits the orthodontist to rapidly and easily modify the force applied. Typically, the patient repeatedly visits the orthodontist over a period of time permitting the orthodontist to perform incremental adjustments to the orthodontic hardware to effect appropriate movement of the teeth 16 and 18. Modification of the applied force is one of the most significant adjustments performed by the orthodontist. The direction of the applied force is also very important, as will be discussed in greater detail hereinafter. To vary the effective length of the orthodontic device 10 to change the applied force, the orthodontist simply removes the spring element 10 from its attachment points and makes the appropriate modification in the primary bend 70. Given sufficient experience, the orthodontist can estimate by "feel" the amount of force applied by a particular configuration of the primary bend 70. The orthodontist increases and decreases the radius of curvature and/or the shape of the primary bend 70 to vary the effective length and, hence the force applied by the device 10. Other practitioners may use a force gauge when performing the adjustment, as is known in the art. The primary bend 70 may be adjusted between a first position, having a minimum radius of curvature, and a second position, having a maximum radius of curvature, depending upon the patient's anatomy and the force desired.

The effective length may be modified to provide an applied force to the teeth 16 and 18 in a range from about one-half ounce to ten ounces. Several basic sizes or models of the device 10 may be provided. For example, to accommodate all patients, three basic models of the device 10 may be used. Each model or size is configured to apply the required force appropriate to effect proper movement of the teeth 16 and 18. However, the number of basic models may be suitably increased or decreased to accommodate the required range of applied force in different patients and in various degrees of malocclusions. This is significant from a cost and inventory standpoint since it is relatively simple and cost-effective to have three models of the device 10 in stock at all times. Other force element devices, such as the device described above in the Vogt patent, would require at least nine different lengths, each of differing widths with each variation having differing aperture sizes. The number of permutations would be extremely high and use of such a device would require an expensive and cumbersome inventory.

The choice of models or size (length) of the orthodontic device 10 is also determined by the size of the patient's mouth, generally depending whether the patient is a child or an adult or if teeth have been extracted. Since adults have larger jaws, the jaws of an adult patient opens through a wider arc than the jaws of a child. Accordingly, a device 10 of greater length may be required.

Note, that the configuration and number of strands forming the wire of the spring element 10 may also be a factor in determining the range of force applied in each of the models of the orthodontic device. For example, as the number of strands of wire used to form the spring element 10 is increased, the stiffness of the spring element is decreased, thus the applied force is decreased for that particular configuration. Even though the number of strands of wire forming the spring element 10 may vary, the outside diameter preferably remains constant within the limits of the inside diameter of the auxiliary molar tube 40, regardless of the application. Thus, all of the models of the orthodontic device 10 may have identical outside diameters and are received within the existing auxiliary molar tube 40 without requiring any modification to existing orthodontic hardware. Preferably, the spring element 10 is constructed from between five to nine strands of wire wrapped around a single strand. However, the number of wrapping strands and the number of core strands may vary according to the force required and manufacturing constraints.

Figure 4A:
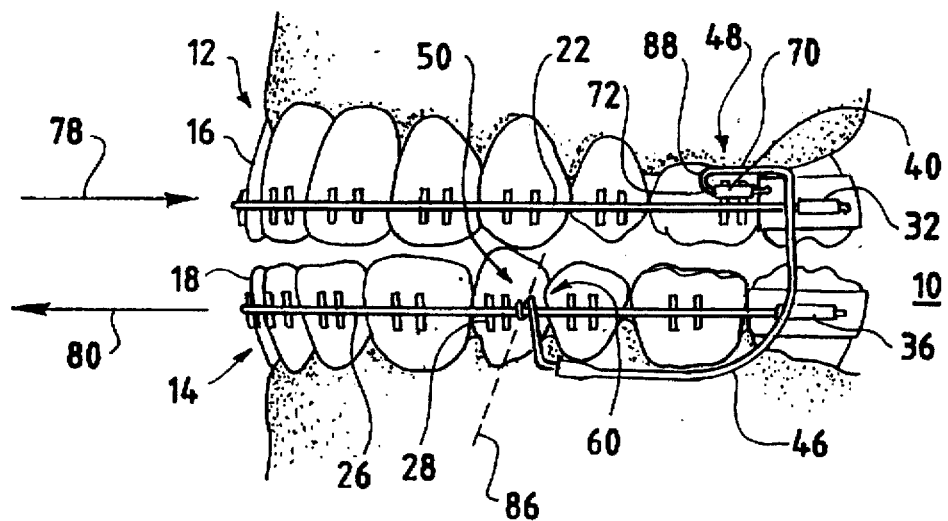
FIGS. 4A and 4B are schematic representations of a closed and open mouth, respectively, particularly illustrating placement of a loop portion of the spring element relative to the lower archwire.
Figure 4B:
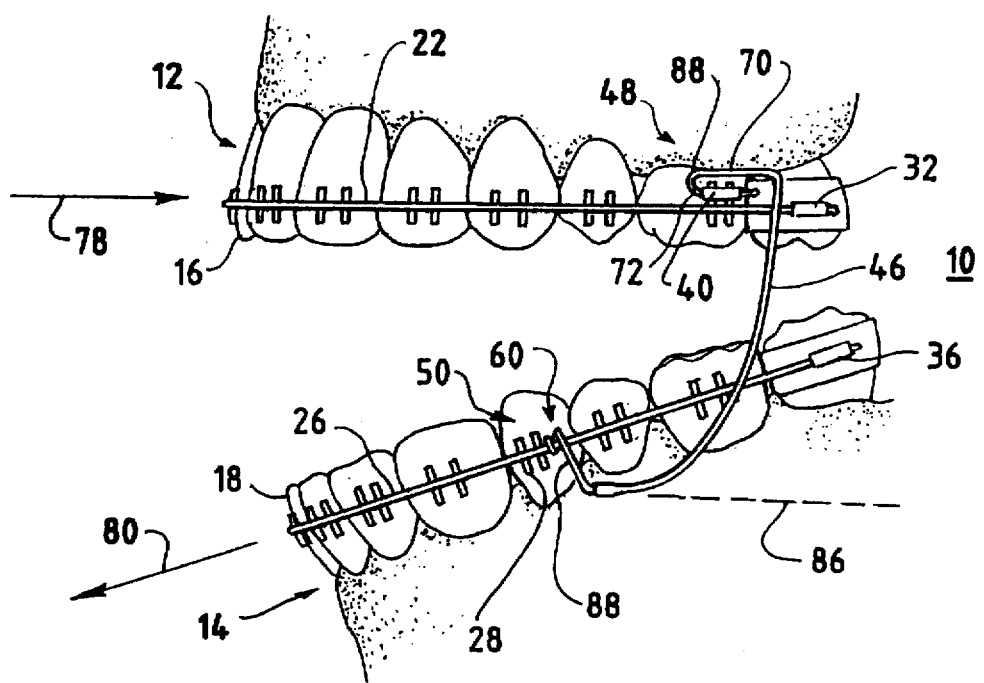

Referring now to FIGS. 1 and 4A–4B, FIGS. 4A–4B are schematic representations of the mouth of a hypothetical patient with the patient's jaws in a closed and open position, respectively. In the closed position, shown in FIG. 4A, it can be seen that the primary bend 70 permits the spring element 10 to gently curve or spiral around to where the attachment point on the second end portion 50 connects to the archwire 26. The lower archwire 26 is the lower attachment means while the auxiliary molar tube 40 is the upper attachment means. The spring element 10 is under spring stress since it is resiliently compressed when attached. Such compression results in a translational force applied to the molars tending to force the upper teeth backward and the lower teeth forward, as shown by arrows 78 and 80, respectively (FIG. 4A–4B).

Note that the loop 60 that terminates the second end portion 50 has an axis 86 or tangent that is at an angle relative to the lower archwire 26. For example, the axis 86 may be at an angle of about forty-five degrees relative to the lower archwire 26 when the jaws are in the closed position, shown in FIG. 4A. In the closed position of FIG. 4A, the loop 60 abuts against the vertical supports 28, thus providing force tending to move the lower teeth 18 forward and the upper teeth 16 backward, as shown by arrows 78 and 80. Note that the axis of the loop 60 is generally angled or canted relative to the lower archwire 26. The axis 86 or tangent of the loop 60 is permitted to move or rotate relative to the lower archwire 26 as the jaws 12 and 14 separate. Such rotation changes the angle of the axis 86 with respect to the lower archwire 26, as is shown in FIG. 4B. The axis 86, and hence the loop 60 may rotate through an angle of about ninety degrees during the full range of mandibular movement from the closed position to the fully open position of the jaws 12 and 14.

In FIG. 4B, in the open position, the spring element 10 is still under resilient stress and still applies substantially continuous translational force to the teeth 16 and 18. Again, the loop 60 abuts longitudinally against the vertical supports 28, thus providing force tending to move the lower teeth 18 forward and the upper teeth 16 backward, as indicated by arrows 78 and 80.

Note that in FIG. 4B, the position of the loop 60 and, hence the axis 86, relative to the lower archwire 26 is no longer at an approximate minus forty-five degree angle relative to the lower archwire 26. In this open configuration, the axis 86 is rotated in accordance with rotation of the loop 60 about the lower archwire 26. The loop 60 is capable of rotation about the lower archwire 26 since the loop is not fixedly attached to the lower archwire. The loop 60 freely rotates about the lower archwire 26 while positively engaging the lower archwire within the loop. Such rotation of the loop 60 about the lower archwire 26 permits the spring element 10 to apply substantially continuous force to the teeth 16 and 18 whether the jaws of the patient are in the open position or the closed position.

Note that as the loop 60 rotates about the lower archwire 26 during the full range of mandibular movement, the loop may also slide forward and backward along the lower archwire between the two "stops" or vertical supports 28 between which the loop is positioned. Additionally, the force applied by the spring element 10 is substantially continuous throughout almost all of the full range of mandibular movement.

Note that in the closed position shown in FIG. 4A, the axis 86 is canted backwardly at about a minus forty-five degree angle. Thus, when the jaws are moved from the most closed position to the most open position, the axis 86 rotates from minus forty-five degrees to about plus forty-five degrees. Thus, a ninety degree rotation of the loop 60 occurs. Note that in the FIGS. 4A-4B, the angles are not drawn to scale.

The loop 60 also includes a loop bend 87 which is substantially within the plane of the body portion 48. The loop bend 87 in conjunction with the primary bend 70 is operative to vary the effective length of the spring element 10. Thus, orthodontist adjusts and configures the primary bend 70 and the loop bend 80 to vary the effective length, and hence the applied force.

Another important feature of the loop 60 is that it permits the plane of the body portion 46 to remain essentially parallel to the plane of the patient's cheek. This is extremely important for reasons of user comfort. Known orthodontic devices, such as those described above, tend to budge outward into the patient's cheek as the patient chews. Thus, each time the patient closes his or her mouth, the device protrudes into the cheek. This may cause discomfort and annoyance. Additionally, such movement of known devices may allow the patient to inadvertently bite the device causing possible damage to the device and to the patient's teeth. Due, in part, to rotation of the loop 60, all flexing and resilient deformation of the spring element 10 in the present novel device occurs in a plane parallel to the cheek the patient. According, the orthodontic device 10 remains substantially parallel to the cheek and parallel to the upright surfaces or side edges of the teeth 16 and 18 as the patient chews, and does not protrude or bulge into the cheek.

Figure 5:
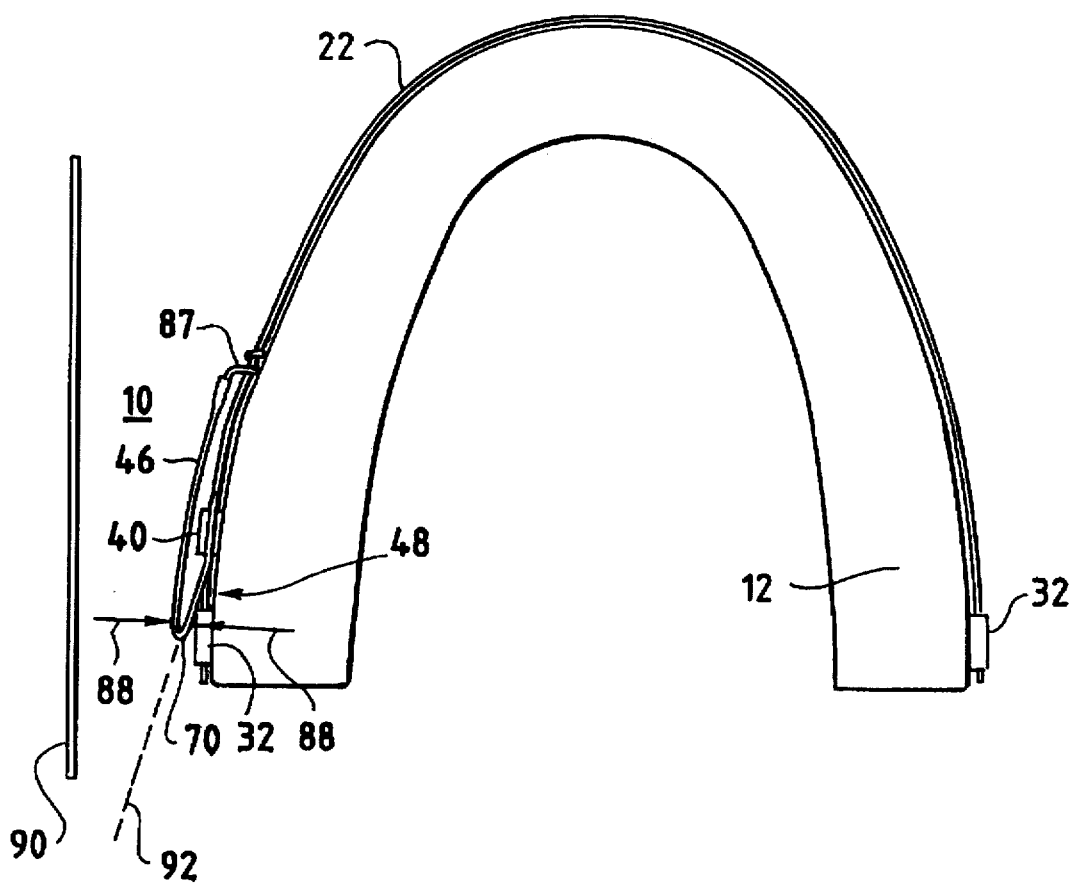
FIG. 5 is a top view of an upper jaw or arch particularly illustrating the profile of the spring element relative to the plane of the cheek of the patient.

Referring now to FIG. 5, a top view of the upper jaw or arch 12 is shown particularly illustrating the profile of the spring element 10 relative to the plane of the cheek, indicated as reference numeral 90. Another reason why the plane of the body portion 46 remains substantially parallel to the plane 90 of the cheek is that the spring element 10 includes an additional critical bend or secondary bend 88. The secondary bend 88 is disposed proximal to the primary bend 70. The secondary bend 88 is substantially perpendicular to the plane of the primary bend 70 and may be oriented laterally, either toward or away from the cheek of the patient, as is indicated by the arrows 88. The secondary bend 88 is effective to pivot the plane of the body portion 46 so that it is operatively disposed in a plane substantially parallel to the plane defined by the cheek 90 of the patient. The secondary bend 88 is configured to vary the plane of the body portion 46 from between minus forty degrees to plus forty degrees relative to the plane of the cheek 90 of the patient, as shown by line 92.

Referring now to FIGS. 1 and 2A-2B, it is noted that the loop 60 may formed as an open loop, a spiral loop, or a substantially closed loop. As shown in the illustrated embodiment, the loop 60 is preferably a spiral loop such that the extreme end of the loop does not contact itself. Thus, the loop 60 has a partially open portion 94 (FIGS. 2A and 2B) such that the open portion is "skewed" away from itself and does not reside in the plane of the loop. This permits the orthodontist to easily and quickly attach and detach the loop 60. The orthodontist manipulates the angle of the loop 60 so that the open portion 94 of the loop 60 engages the lower archwire 26. This essentially "captures" the archwire within the loop 60. Once in position, the loop 60 cannot become disengaged from the lower archwire 26 since the force exerted by the spring element 10 between the loop 60 and the vertical supports 28 (FIG. 1) against which it abuts, tends to urge the open portion 94 of the loop away from the lower archwire 26, thus preventing disengagement. Only intentional and specific manipulation of the orthodontic device 10 permits removal of the loop 60 from the lower archwire 26. As discussed above, as the patient chews, the loop 60 rotates about the lower archwire 26. During such rotation, the open portion 94 of the loop 60 is at all times urged away from the lower archwire 26 so as not to be disengaged therefrom. The partially open spiral loop 60 configuration is preferred since a fully closed loop would require the additionally step of opening the loop with a suitable tool for removal and crimping or closing the loop after installation.

Note that loop 60 may be separately but fixedly attached to the spring element 10. As shown in FIGS. 2A-2B in dashed lines, a crimped cap portion 98 may connect the loop 60 to the spring element 10. However, any suitable form of connector may connect the loop 60 to the spring element 10.

Referring now to FIGS. 1 and 3, note that the straight segment 72 received within the auxiliary molar tube 40 is received within a forward end 100 (FIG. 3) of the auxiliary molar tube rather than within a rearward end 102 (FIG. 3). This is a significant feature for at least two reasons. First, attachment to the forward end 100 of the auxiliary molar tube 40 facilitates easy an rapid attachment since attachments further back in the mouth of the patient are more difficult to perform due to space constraints.

Second, attachment at the forward end 100 of the auxiliary molar tube 40 permits the primary bend 70 to spiral backward avoiding intersecting an imaginary line connecting the upper and lower attachment points (i.e., the auxiliary molar tube 40 and the loop 60). This configuration allows for easy adjustment of the effective length of the spring element 10 where such adjustment does not create a situation where the spring element impinges upon the teeth, the existing orthodontic appliances, or the soft tissue of the patient's mouth. This configuration, having a backward spiral, permits use of a relatively long length of spring element material 10 relative to the amount of space available in the patient's mouth so the patient is permitted a full range of mandibular movement. This significantly increases the range through which the orthodontic device 10 applies substantially continuous force to the teeth 16 and 18. Because the first end 48 of the spring element 10 is received directly within the auxiliary molar tube 40, the mechanics of the spring element differ from that of known spring-type orthodontic devices. Prior art devices are typically pinned to the molar tube from the outer aspect or the rearward end 102 (FIG. 3) of the molar tube. Alternately, these prior art devices may be anchored to an archwire which connects the molar to the adjacent tooth. Such a configuration creates a "tipping" force or rotational moment about the center of resistance of the tooth. The center of resistance of the molar tooth is below the level of the gum and toward the root of the tooth. Such tipping force is usually undesirable if only translational force need be applied. Prior art devices counteract the effect of the tipping force by stabilizing that tooth with the archwire connected to adjacent teeth. Thus, known prior art devices must always stabilize the anchor tooth by rigid connection to the archwire.

Since the spring element 10 of the present device is attached directly into the auxiliary molar tube 40 and applies a spring force to the tooth, a "lever arm" is formed. The opposite end 50 (second end—FIG. 1) is attached to the lower archwire 26 via the loop 50, and raising or lowering the lever arm creates a "couple" which produces a force moment balancing the tipping force. The spring element may be configured so that it only produces translational forces (arrows 78 and 80 of FIG. 4A–4B) on the teeth 16 and 18 without producing tipping or rotational forces. If a tipping force is desired, the spring element 10 may also be configured to provide it by varying the ratio of compressive force to lifting force effected by changing the length and shape of the spring element 10, as described. This is significant since the orthodontic device 10 may be affixed to a tooth that need not be stabilized by connection to an archwire. This is useful where the primary teeth are being lost and replaced with permanent teeth.

Referring now to FIG. 1, in operation, the orthodontist determines the desired effective length of the spring element 10 and adjusts the shape of the primary bent 70 and the loop bend 88 to correspond to the desired effective length. The effective length is operative to vary the applied forced directed toward the upper and lower teeth 16 and 18. Once the primary bend 70 and the loop bend 87 have been configured, the orthodontist places the spiral loop 60 proximal the lower archwire 26 so that the loop engages the lower archwire and cannot be inadvertently removed therefrom. The spiral loop 60 is inserted from outside of the mouth so that the open portion of the loop engages the lower archwire 26. The spring element 10 is then upwardly rotated so that the spiral loop 60 captures the lower archwire 26, thus rotatably locking the loop 60 about the lower archwire. The body portion 46 of the spring element 10 is then rotated into the plane of the patient's cheek essentially permitting the entire spring element 10 to be positioned within the mouth of the patient. Next, the orthodontist directly connects the straight portion 72 of the spring element 10 to the auxiliary molar tube and bends the end of the straight segment protruding through the tube, so as to lock the spring element in place. The plane of the body portion 46 may then be adjusted to be parallel to the plane of the patient's cheek by appropriate modifications of the secondary bend 88.

Specific embodiments of an orthodontic device and method according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An orthodontic device for wearing in a mouth of a patient, the device adapted for attachment between an upper attachment means secured to at least one maxillary tooth of a plurality of maxillary teeth and a lower attachment means secured to at least one mandibular tooth of a plurality of mandibular teeth, the device proximal a cheek of a patient, said device comprising:

a single flexible resilient spring element having a generally curved body portion configured to be inserted in the patient's mouth so as to lie in a plane defined by the cheek of the patient;

the spring element having first and second oppositely disposed end portions, said first end portion configured to be directly attached to at least one of the upper and lower attachment means, said second end portion configured to be directly attached to the other of the upper and lower attachment means;

the spring element being operative to directly produce an applied force between the upper and lower attachment means when attached thereto, so as to displace the maxillary teeth relative to the mandibular teeth;

the first end portion having a primary bend disposed substantially within the plane of the body portion and operative to vary the effective length of the spring element, the variation in the effective length of the spring element configured to vary the applied force directed to the maxillary and mandibular teeth;

the second end portion terminating in a loop portion configured to attach to the other of the corresponding attachment means; and said first end portion further including a secondary bend disposed proximal the primary bend and formed substantially perpendicular to the plane of the body portion, the secondary bend effective to pivot the plane of the body portion so that the body portion is operatively disposed in a plane substantially parallel to the plane defined by the cheek of the patient.

2. The device according to claim 1 wherein the upper and lower attachment means are existing attachment means attached to the maxillary and mandibular teeth of the patient, respectively, said spring element removably attaching directly to a tube means associated with at least one of the upper and lower existing attachment means such that additional connectors are not required to directly attach the spring element to the existing attachment means.

3. The device according to claim 2 wherein the tube means has forward and rearward ends, said spring element removably attachable directly to the forward end of the tube means forming the primary bend having a spiral configuration extending toward the rearward end of the tube means and toward the other of the upper and lower existing attachment means, said primary bend and said curved body portion permitting the spring element to be formed from an increased length of material, said increased length operative to provide an effective length such that variation of the effective length varies the force applied to the teeth.

4. The device according to claim 1 wherein the spring element applies substantially a translational force directed between the mandibular teeth and the maxillary teeth, said spring element configured such that rotational force directed toward teeth associated with at least one of the upper and lower attachment means is substantially eliminated.

5. The device according to claim 1 wherein the force applied by the spring element is substantially continuous throughout a full range of movement defined by an angular position of the maxillary teeth relative to the mandibular teeth.

6. The device according to claim 1 wherein adjustment of the primary bend between a first position and a second position varies the applied force from about between one-half ounce to ten ounces.

7. The device according to claim 1 wherein the secondary bend is configured to vary the plane of the body portion from between about minus forty degrees to plus forty degrees relative to the plane of the cheek of the patient.

8. The device according to claim 1 wherein the spring element is formed from stranded wire.

9. The device according to claim 1 wherein the spring element is formed from solid wire.

10. The device according to claim 1 wherein the spring element is formed from material selected from the group consisting of nickel titanium alloy, nickel chrome alloy, and stainless steel.

11. The device according to claim 1 wherein the spring element is formed from material selected from the group consisting of plastic and fiberglass.

12. The device according to claim 1 wherein the applied force produced by the spring element is decreased by decreasing the effective length of the spring element and is increased by increasing the effective length of the spring element.

13. The device according to claim 1 wherein the loop portion is at least one of an open loop, a spiral loop, and a substantially closed loop, at least one of said loops configured to rotate about the corresponding attachment means, said rotation of the loop permitting the body portion of the spring element to be maintained in a plane parallel to the plane of the cheek of the patient through a full range of mandibular movement.

14. The device according to claim 13 wherein the loop is configured to rotate through an angle of about ninety degrees.

15. The device according to claim 1 wherein the second end further includes a cap portion fixedly attached to the spring element, said cap portion terminating in a loop configured to attach to the other of the corresponding attachment means.

16. The device according to claim 1 wherein the second end further includes a loop bend, the loop bend disposed substantially within the plane of the body portion and disposed proximal the loop portion, the loop bend operative to vary the effective length of the spring element, the variation in the effective length of the spring element configured to vary the applied force directed toward the maxillary and mandibular teeth.

17. The device according to claim 16 wherein the primary bend and the loop bend are configured to vary the effective length of the spring element.

18. An orthodontic device for wearing in a mouth of a patient, the device adapted for attachment between an upper attachment means secured to an upper tooth, and a lower attachment means secured to a lower tooth, the device proximal a cheek of a patient, the device comprising:

a single flexible resilient spring element having a generally curved body portion defined to lie in a plane defined by the cheek of the patient;

the spring element having first and second oppositely disposed end portions, the first end portion configured to directly attach to at least one of the upper and lower attachment means, the second end portion configured to directly attach to the other of the upper and lower attachment means;

the spring element producing an applied force between the upper and lower attachment means operative to displace upper teeth relative to lower teeth;

the first end portion having a primary bend, disposed substantially within the plane of the body portion and operative to vary the effective length of the spring element, the variation in the effective length of the spring element configured to vary the applied force directed to the upper and lower teeth;

the second end portion having connecting means configured to attach to the other of the corresponding attachment means; and the first end portion further including a secondary bend disposed proximal the primary bend and substantially perpendicular thereto, the secondary bend effective to pivot the plane of the body portion so that it is operatively disposed in a plane substantially parallel to the plane defined by the cheek of the patent.

19. The device according to claim 18 wherein the connecting means is a loop portion formed proximal the second end portion of the spring element, the loop portion configured to attach to the other of the corresponding attachment means.

20. The device according to claim 18 wherein the upper and lower attachment means are existing attachment means attached to the upper tooth and the lower tooth of the patient, respectively, said spring element configured to be removably attachable directly to a spring element receiving means associated with at least one of the upper and lower existing attachment means such that additional connectors are not required to directly attach the spring element to the existing attachment means.

21. A method for applying a force between maxillary teeth and mandibular teeth to effect movement of the teeth, the maxillary teeth and mandibular teeth having upper and lower attachment means affixed thereto, the method comprising the steps of:

a) determining a desired effective length of a single flexible resilient spring element, said spring element configured to directly attach between the upper and lower attachment means, the spring element having a generally curved body portion with first and second oppositely disposed end portions;

b) adjusting a primary bend corresponding to the first end portion, the primary bend operative to vary the effective length of the spring element so that the applied force directed to the maxillary and mandibular teeth is varied in accordance with the effective length;

c) placing a loop portion corresponding to the second end portion of the spring element about at least one of the upper and lower attachment means; and d) operatively connecting the first end portion to the other of the upper and lower attachment means so that the spring element is secured between the upper and lower attachment means.

22. The method according to claim 21 wherein the first end portion further includes a secondary bend, the secondary bend disposed proximal the primary bend and substantially perpendicular thereto, the secondary bend effective to pivot the plane of the body portion so that it is operatively disposed in a plane substantially parallel to the plane defined by the cheek of the patient.

23. The method according to claim 21 wherein placement of the plane of the body portion in a parallel orientation relative to the plane of the cheek of the patient permits flexing of the body portion parallel to the cheek so that the device does not protrude into the cheek when the mouth of the patient is moved between a fully open position and a fully closed position and between a lateral position and a protrusive position.

24. The method according to claim 21 wherein the spring element is formed from stranded wire.

25. The method according to claim 21 wherein the loop portion is one of a spiral loop, an open loop, and a substantially closed loop.

26. The method according to claim 21 further including the step of forming a loop bend in the spring element, the loop bend disposed substantially within the plane of the body portion and disposed proximal the loop portion, the loop bend operative to vary the effective length of the spring element, the variation in the effective length of the spring element configured to vary the applied force directed toward the maxillary and mandibular teeth.

27. A method for applying a force between maxillary teeth and mandibular teeth to effect movement of the teeth, the maxillary teeth and mandibular teeth having upper and lower attachment means affixed thereto, the method comprising the steps of:

a) determining a desired effective length of a single flexible resilient spring element, said spring element configured to directly attach between the upper and lower attachment means, the spring element having a generally curved body portion with first and second oppositely disposed end portions;

b) adjusting a primary bend corresponding to the first end portion, the primary bend operative to vary the effective length of the spring element so that the applied force directed to the maxillary and mandibular teeth is varied in accordance with the effective length;

c) placing a loop portion corresponding to the second end portion about at least one of the upper and lower attachment means;

d) operatively connecting the first end portion to the other of the upper and lower attachment means so that the spring element is secured between the upper and lower attachment means;

e) adjusting a secondary bend in the spring element, the secondary bend disposed proximal the primary bend and formed substantially perpendicular to the plane of the body portion, the secondary bend effective to pivot the plane of the body portion so that the body portion is operatively disposed in a plane substantially parallel to the plane defined by the cheek of the patient.

28. The method according to claim 27 the loop portion is one of a spiral loop, an open, loop, and a substantially closed loop.

29. The method according to claim 28 further including the step of forming a loop bend in the spring element, the loop bend disposed substantially within the plane of the body portion and disposed proximal the loop portion, the loop bend operative to vary the effective length of the spring element, the variation in the effective length of the spring element configured to vary the applied force directed toward the maxillary and mandibular teeth.

* * * * *